United States Patent
West, Jr. et al.

(10) Patent No.: US 7,686,810 B2
(45) Date of Patent: Mar. 30, 2010

(54) SUTURE SEPARATION AND ORGANIZATION DEVICES FOR USE WITH GRAFT TENSIONING DEVICE

(75) Inventors: Hugh S. West, Jr., Salt Lake City, UT (US); John R. West, Cincinnati, OH (US); Mark Dallara, Tampa, FL (US); Jeff Bennett, Pottstown, PA (US)

(73) Assignee: HS West Investments, LLC, Salt Lake City, UT (US)

( * ) Notice: Subject to any disclaimer, the term of this patent is extended or adjusted under 35 U.S.C. 154(b) by 571 days.

(21) Appl. No.: 10/786,186

(22) Filed: Feb. 25, 2004

(65) Prior Publication Data

US 2005/0049597 A1      Mar. 3, 2005

Related U.S. Application Data

(63) Continuation-in-part of application No. 10/651,671, filed on Aug. 29, 2003, now Pat. No. 7,118,578.

(51) Int. Cl.
*A61B 17/58*  (2006.01)

(52) U.S. Cl. .................................................. 606/88

(58) Field of Classification Search .......... 606/73, 606/88, 96, 102, 103, 232, 233, 69, 139, 606/148, 138, 280; 623/13.11–13.14
See application file for complete search history.

(56) References Cited

U.S. PATENT DOCUMENTS

| | | | |
|---|---|---|---|
| 3,869,932 A * | 3/1975 | Fletcher ....................... 474/46 |
| 3,896,500 A | 7/1975 | Rambert et al. | |
| 4,301,551 A | 11/1981 | Dore et al. | |
| 4,400,833 A | 8/1983 | Kurland | |
| 4,467,478 A | 8/1984 | Jurgutis | |
| 4,529,147 A * | 7/1985 | Bull et al. ................ 242/156.2 |
| 4,590,928 A | 5/1986 | Hunt et al. | |
| 4,597,766 A | 7/1986 | Hilal et al. | |
| 4,605,414 A | 8/1986 | Czajka | |
| 4,649,916 A | 3/1987 | Frimberger | |
| 4,668,233 A | 5/1987 | Seedhom et al. | |
| 4,692,116 A * | 9/1987 | Filhol ........................ 433/225 |
| 4,712,542 A * | 12/1987 | Daniel et al. .................. 606/96 |
| 4,739,751 A | 4/1988 | Sapega et al. | |
| 4,744,793 A | 5/1988 | Parr et al. | |
| 4,772,286 A | 9/1988 | Goble et al. | |
| 4,773,417 A | 9/1988 | Moore et al. | |
| 4,834,752 A | 5/1989 | Van Kampen | |
| 4,870,957 A | 10/1989 | Goble et al. | |
| 4,922,897 A | 5/1990 | Sapega et al. | |

(Continued)

*Primary Examiner*—Eduardo C Robert
*Assistant Examiner*—Tara R George
(74) *Attorney, Agent, or Firm*—Workman Nydegger

(57) ABSTRACT

Suture separation and organization devices for use in a tissue graft tensioning system. The inventive devices help to separate and organize a plurality of suture strands that extend away from a bone tunnel of a patient's leg during joint repair surgery (e.g., while repairing or replacing the anterior cruciate ligament ("ACL")). The suture separation and organization device may comprise one or more elongate bodies, or a one-piece body, comprising a plurality of suture retention recesses or protrusions disposed on a perimeter of a body. The suture separation and organization device also includes recesses or passages adapted to receive corresponding posts of a graft tensioning device. In this way, the suture separation and organization device can be removably attached to the graft tensioning device.

15 Claims, 10 Drawing Sheets

U.S. PATENT DOCUMENTS

| | | |
|---|---|---|
| 4,927,421 A | 5/1990 | Goble et al. |
| 4,950,270 A | 8/1990 | Bowman et al. |
| 4,950,271 A * | 8/1990 | Lewis et al. ............... 606/102 |
| 4,969,895 A | 11/1990 | McLeod et al. |
| 4,997,433 A | 3/1991 | Goble et al. |
| 5,037,426 A | 8/1991 | Goble et al. |
| 5,071,420 A | 12/1991 | Paulos et al. |
| 5,108,433 A | 4/1992 | May et al. |
| 5,129,902 A | 7/1992 | Goble et al. |
| 5,139,520 A | 8/1992 | Rosenberg |
| 5,147,362 A | 9/1992 | Goble |
| 5,207,703 A * | 5/1993 | Jain ........................... 606/232 |
| RE34,293 E | 6/1993 | Goble et al. |
| RE34,762 E | 10/1994 | Goble et al. |
| 5,507,750 A | 4/1996 | Goble et al. |
| 5,562,668 A | 10/1996 | Johnson |
| 5,630,820 A | 5/1997 | Todd |
| 5,713,897 A | 2/1998 | Goble et al. |
| 5,860,980 A * | 1/1999 | Axelson et al. ............... 606/88 |
| 5,935,130 A | 8/1999 | Kilpela et al. |
| 5,964,764 A | 10/1999 | West, Jr. et al. |
| 5,980,473 A | 11/1999 | Korakianitis et al. |
| 6,001,106 A | 12/1999 | Ryan et al. |
| 6,036,694 A | 3/2000 | Goble et al. |
| 6,066,142 A * | 5/2000 | Serbousek et al. ............ 606/96 |
| 6,171,310 B1 * | 1/2001 | Giordano et al. .............. 606/60 |
| 6,279,415 B1 | 8/2001 | Chance et al. |
| 6,364,885 B1 | 4/2002 | Kilpela et al. |
| 6,547,778 B1 * | 4/2003 | Sklar et al. ...................... 606/1 |
| 6,749,611 B2 * | 6/2004 | Venturini et al. ............... 606/54 |
| 7,160,285 B2 * | 1/2007 | Sklar et al. ...................... 606/1 |
| 2004/0204717 A1* | 10/2004 | Fanger et al. .................. 606/96 |
| 2004/0254593 A1* | 12/2004 | Fallin et al. ................. 606/148 |

* cited by examiner

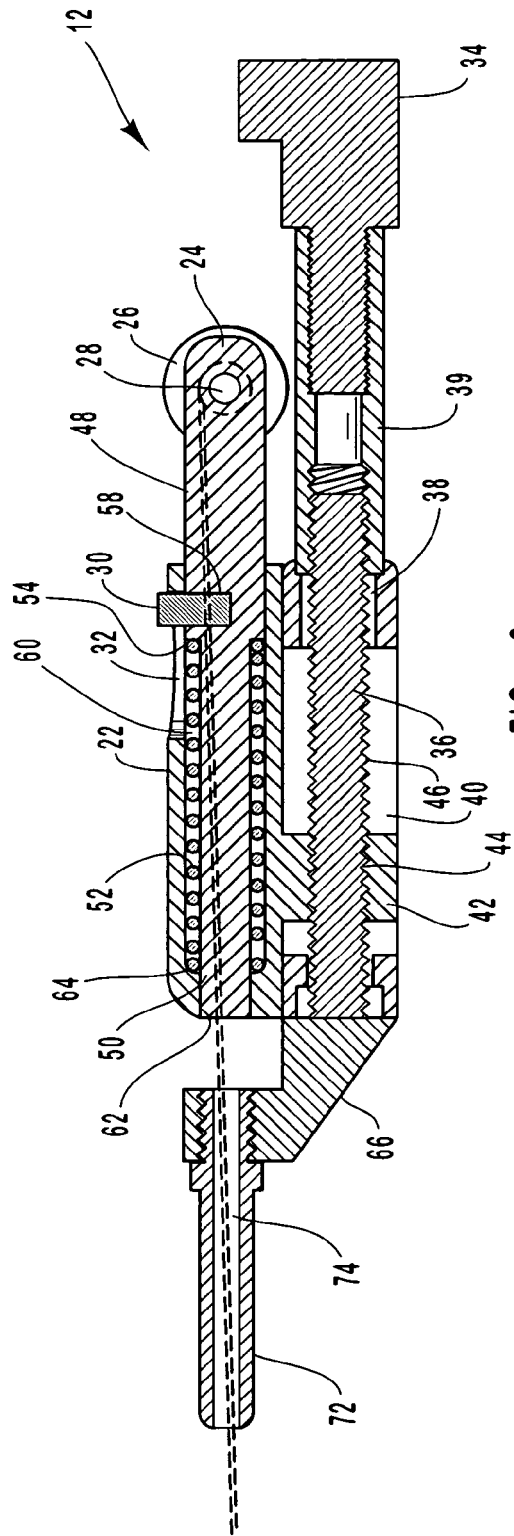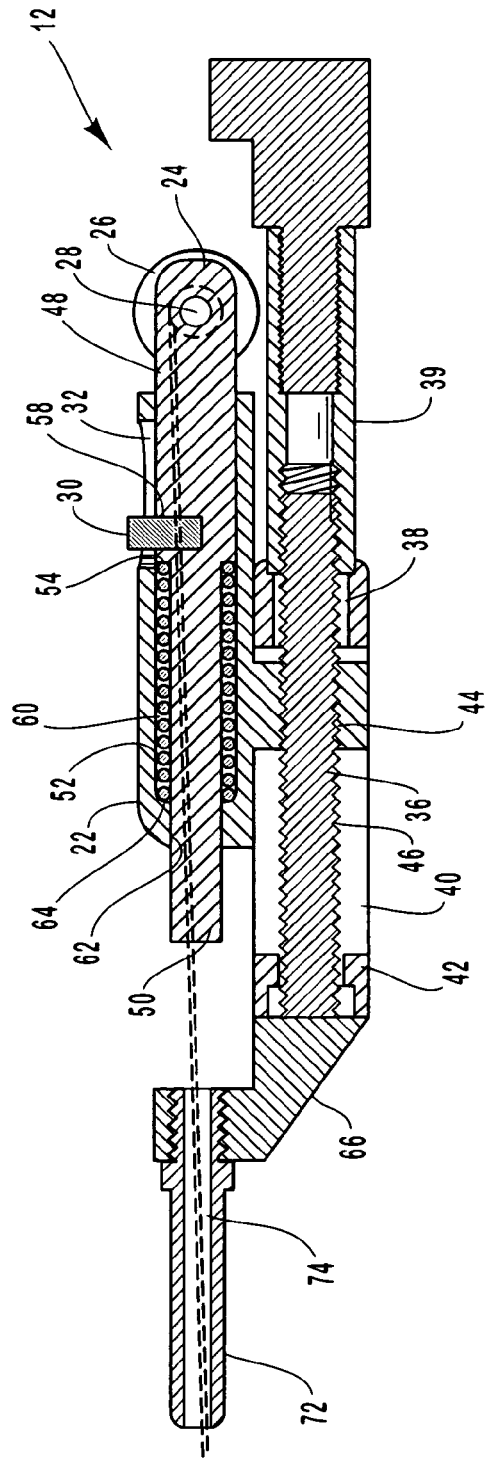

SUTURE SEPARATION AND ORGANIZATION DEVICES FOR USE WITH GRAFT TENSIONING DEVICE

CROSS-REFERENCE TO RELATED APPLICATIONS

This application is a continuation-in-part of U.S. application Ser. No. 10/651,671, filed Aug. 29, 2003 now U.S. Pat. No. 7,118,578. The disclosure of the foregoing application is incorporated herein in its entirety.

BACKGROUND OF THE INVENTION

1. The Field of the Invention

The present invention is in the field of graft tensioning devices used in joint repair surgery, such as reconstruction of the anterior cruciate ligament (ACL). More particularly, the invention relates to suture separation and organization devices for use with graft tensioning devices.

2. The Relevant Technology

Graft tension in ACL reconstruction is recognized as an important factor in the clinical outcome of the ACL reconstruction procedure. Grafts that are too loose may be unstable, and grafts that are too tight may greatly restrict motion of the knee. Publications that have emphasized the need for adequate tensioning of the graft include Markolf et al., "Biomechanical Consequences of Replacement of the Anterior Cruciate Ligament With a Patellar Ligament Allograft. Part Two: Forces in the Graft Compared with Forces in the Intact Ligament," *J. Bone Joint Surg. Am.*, 78:11, 1728-34 (November 1996); Tohyama et al., "Significance of Graft Tension in Anterior Cruciate Ligament Reconstruction. Basic background and clinical outcome," *Knee Surg Sports Traumatol. Arthroscopy*, 6 Suppl. 1, S30-7 (1998); Andersen et al., "Review on Tension in the Natural and Reconstructed Anterior Cruciate Ligament," *Knee Surg. Sports Traumatol. Arthroscopy*, 2:4, 192-202 (1994); Yasuda et al., "Effects of Initial Graft Tension on Clinical Outcome After Anterior Cruciate Ligament Reconstruction. Autogenous Doubled Hamstring Tendons Connected in Series of Polyester Tapes," *Am. J. Sports Med.*, 25:1, 99-106 (January 1997). The foregoing publications are incorporated herein by reference.

Devices used to apply a known load to a soft tissue graft are set forth in U.S. Pat. No. 4,712,542; U.S. Pat. No. 5,037,426; U.S. Pat. No. Re 34,762; U.S. Pat. No. 5,713,897; U.S. Pat. No. 5,507,750; and U.S. Pat. No. 5,562,668. For purposes of disclosing mechanisms for applying a known load or tension onto a soft tissue graft, the foregoing patents are incorporated herein by reference.

A study by Hamner et al. has added to the understanding of graft tension by demonstrating that unequal tension in the individual strands of the soft tissue graft can result in significant losses in total graft strength and stiffness. Hamner et al., "Hamstring Tendon Grafts for Reconstruction of the Anterior Cruciate Ligament: Biomechanical Evaluation of the Use of Multiple Strands and Tensioning Techniques," *J. Bone Joint Surg. Am.*, 81:4, 549-57 (April 1999). Hamner et al. found that tensioning the soft tissue strands by hand would result in equalization of the load borne by each strand, and that this method was not effective in equalizing the load on the strands, which led to an ultimate graft strength that was not significantly greater than the strength of the individual strands taken alone.

Apparatus and methods for separately applying a load to and conditioning different strands of a multiple-strand soft tissue graft are disclosed in U.S. application Ser. No. 09/711, 488, filed Nov. 13, 2000 in the name of Hugh S. West, Jr. and John R. West and entitled "Apparatus and Methods for Independently Conditioning and Pretensioning a Plurality of Ligament Grafts During Joint Repair Surgery". For purposes of disclosure, the foregoing application is incorporated by reference. The apparatus and methods disclosed in the foregoing application represent a major breakthrough in joint repair apparatus and techniques.

Notwithstanding the foregoing, there is a continuous need to find improvements to apparatus and methods used during joint repair surgery, particularly in organizing individual suture strands that are attached to a soft tissue graft.

SUMMARY OF THE INVENTION

The invention encompasses suture separation and organization devices that are part of, or that are used in combination with, a soft tissue graft tensioning device. The graft tensioning device is, in turn, used in conditioning and pre-tensioning a multiple-strand soft tissue graft during joint repair surgery, such as in procedures used to replace or augment the anterior cruciate ligament ("ACL").

The suture separation and organization devices disclosed herein are used to separate and organize the individual suture strands attached to the ends of a multiple-strand or looped soft tissue graft. In one aspect, separating and organizing multiple suture strands helps the surgeon identify and keep track of which sutures are attached to which soft tissue graft strands. This, in turn, facilitates the application of a desired load onto each end of the multiple-strand or looped tissue graft. In another aspect, separating and organizing multiple suture strands helps keeps the sutures from obstructing the bone tunnel while securing the soft tissue graft to the bone (e.g., by inserting an interference screw into the bone tunnel).

The suture separation and organization devices according to the invention can have any desired shape or size. In general, they will include a body, a plurality of attachment passages or recesses in said body that are sized and positioned so as to at least partially receive therein corresponding posts of a graft tensioning device, a plurality of suture retention recesses or protrusions disposed on a perimeter of said body that are adapted to retain a plurality of suture strands or groups of suture strands in a desired spaced-apart orientation, and a passageway or recess in said body through which an interference screw can be inserted during joint repair surgery. In one embodiment, the body comprises an elongate body having a gripping head at one end and a chiseled end at another end that facilitates insertion of the elongate body between two or more suture strands. In another embodiment, the body has a first surface preferably that is substantially flat and oriented toward a graft tensioning device when in use, and a second surface oriented toward a bone tunnel in a patient's leg when in use. In a preferred embodiment, each attachment passage or recess is defined by a respective hollow post guide that extends laterally from the second surface of the body so as to maintain a space between the patient's leg and the second surface of the body when the suture separation and organization device is in use.

The suture separation and organization devices disclosed herein may be used in combination with any graft tensioning device known in the art. They are particularly well-suited for use with graft tensioning devices designed to separately condition and pre-tension multiple and/or looped strands of a soft tissue graft. Examples of graft tensioning devices with which the inventive suture separation and organization devices can be used are disclosed in U.S. application Ser. No. 10/651,671, filed Aug. 29, 2003, and U.S. application Ser. No. 09/711,488, filed Nov. 13, 2000, both of which were previously incorporated by reference. The graft tensioning devices disclosed therein include a plurality of independently adjustable tension applicators.

In one embodiment, the suture separation and organization device is removably attachable to an end of the graft tensioning device and/or the patient's leg adjacent to the patient's bone tunnel. In this way, the suture separation and organization device engages, separates and organizes individual suture strands as they, and the tissue graft ends to which they are attached, emerge from the bone tunnel. The suture separation and organization device can be a one-piece unit, or it may comprise multiple pieces or sections that are assembled or separately attached to the graft tensioning device and/or the patient's leg. In an alternative embodiment, the suture separation and organization device can be integrally attached to the tensioning device.

Whether the suture separation and organization device is removably attachable to the tensioning device and/or leg, or whether it forms an integral part of a graft tensioning device, it will generally include or define a central opening through which an interference screw can be inserted and a plurality of channels, grooves or passageways designed to engage, separate and organize the various suture strands that emerge from a bone tunnel during joint repair surgery. The suture separation and organization device may optionally include recesses designed to engage pins that are connected to the patient's bone and designed to engage the graft tensioning device while in use.

These and other advantages and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings, in which:

FIG. 2 is a cross-sectional view of the graft tensioning device of FIG. 1 taken along line 2-2;

FIG. 2A shows the tensioning device of FIG. 2 after compression of the biasing spring to increase to a tensile load exerted by the tensioning piston onto a looped suture attached to a soft tissue graft;

DETAILED DESCRIPTION OF THE PREFERRED EMBODIMENTS

The invention relates to suture separation and organization devices for use with, or that form part of, a graft tensioning device. In one embodiment, the suture separation and organization devices are used with, or form part of, an apparatus suitable for independently conditioning and pre-tensioning a plurality of soft tissue grafts (e.g., two) during joint repair procedures, such as in procedures to replace or augment the anterior cruciate ligament (ACL).

Exemplary suture separation and organization devices are illustrated in FIGS. 7-10, which are discussed in detail below. Prior to introducing and discussion FIGS. 7-10, attention is made to FIGS. 1-6, which depict exemplary graft tensioning devices and systems with which the inventive suture separation and organization devices may be used, or which the inventive suture separation and organization devices may form part of. FIGS. 1-6 and the accompanying discussion are given by way of a background and do not limit the scope of the invention.

Figure 1:
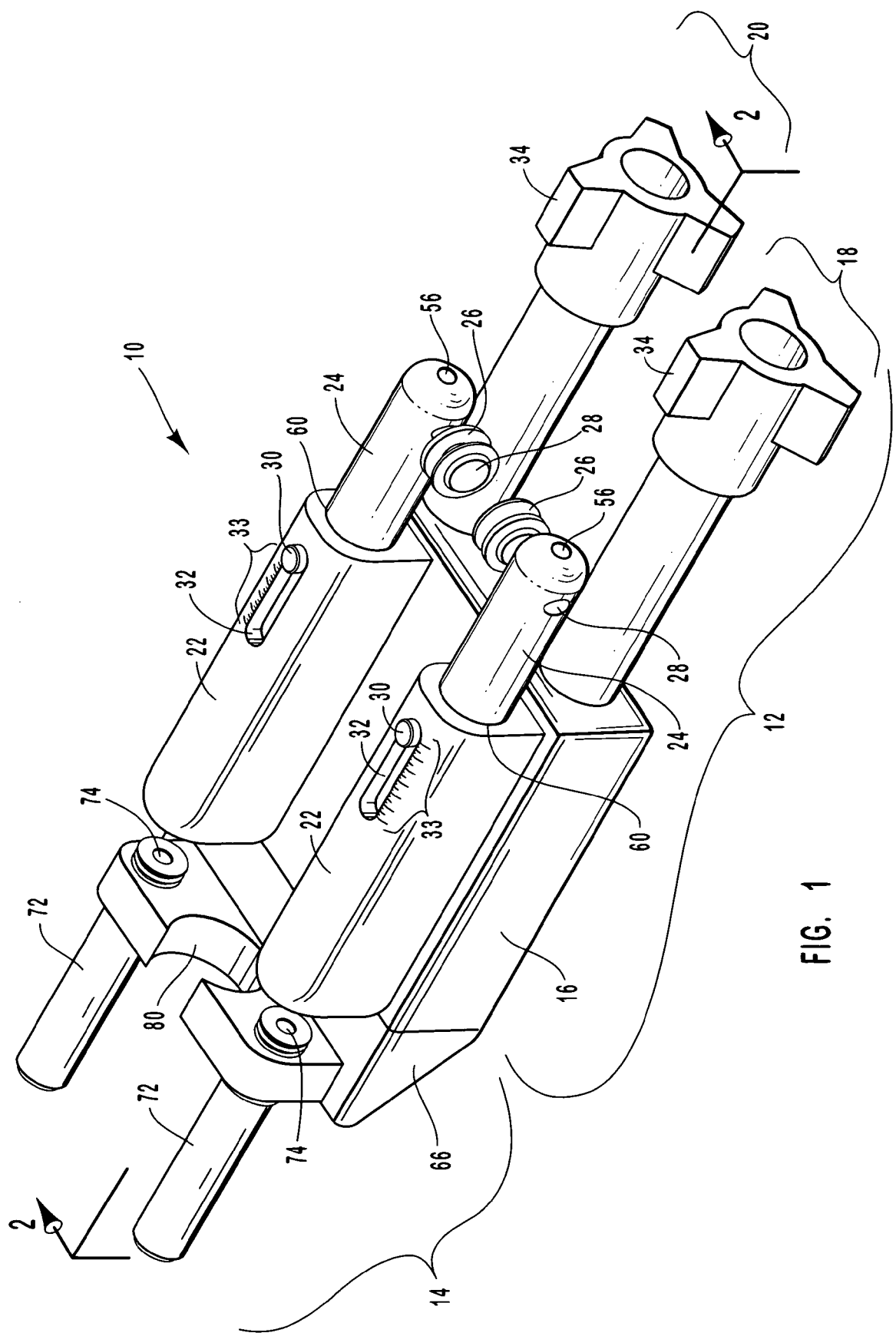
FIG. 1 is a perspective view of a graft tensioning device designed to independently condition and pre-tension a multiple-strand soft tissue graft.
Figure 3:
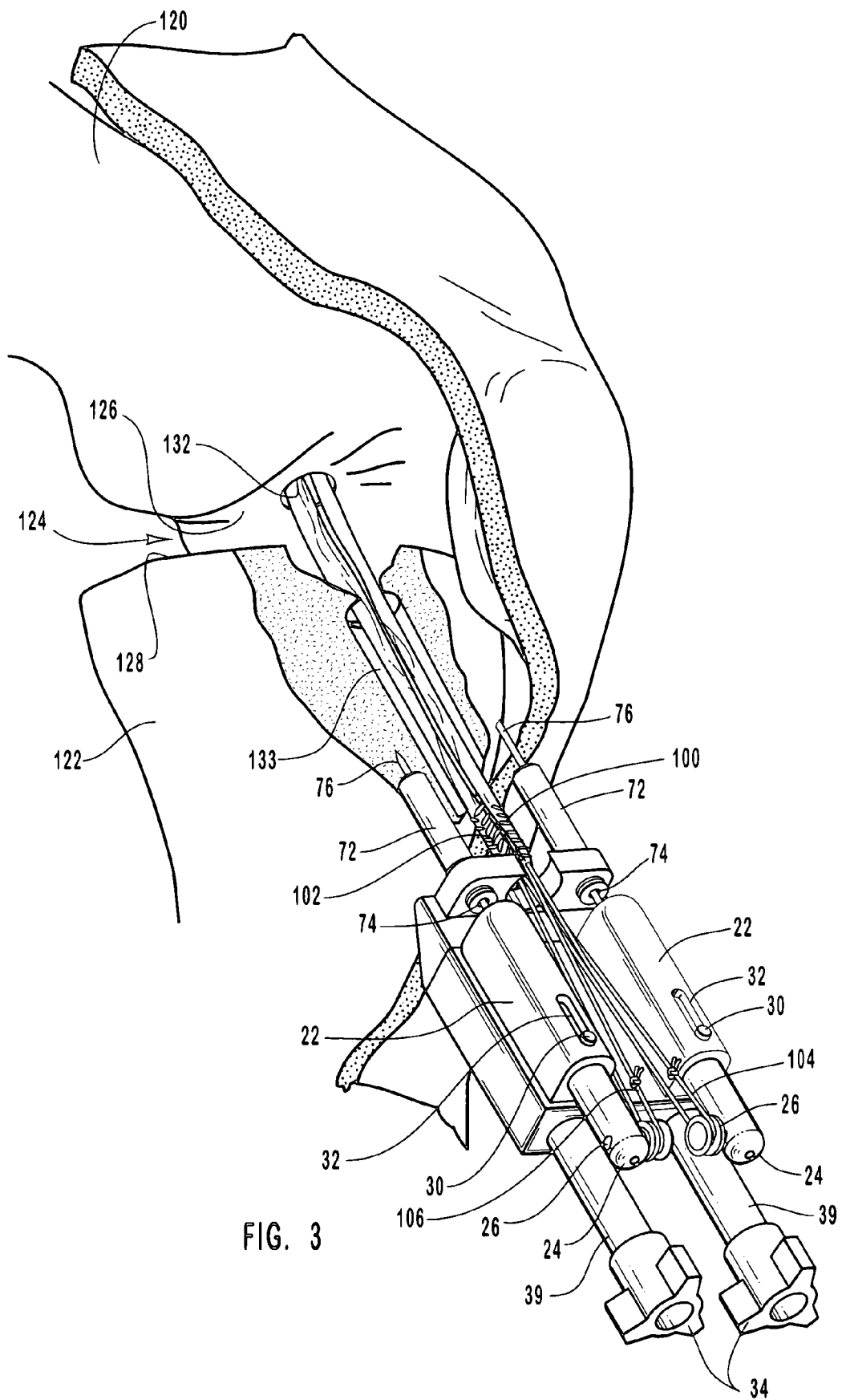
FIG. 3 shows a graft tensioning device attached to a patient's leg during joint repair surgery, with a multiple-strand soft tissue graft emerging from a bone tunnel and tissue graft sutures attached to the tensioning device.

FIGS. 1-3 depict, by way of background, a graft tensioning device 10 capable of independently conditioning and applying tension to two separate soft tissue strands, or groups of strands. Tensioning device 10 is modular, i.e., it includes two separate and detachable substructures or systems, namely a tensioning system 12 and a limb attachment system 14. Tensioning system 12 includes a tensioning block or module 16. Attached to, or associated with, the tensioning module 16 are a first adjustable tension applicator 18 and a second adjustable tension applicator 20, which are essentially mirror images of each other. Each of the first and second adjustable tension applicators 18 and 20 includes a cylinder block or module 22 and a tensioning piston 24 partially disposed within the cylinder module 22. The cylinder module 22 and tensioning piston 24 are able to move relative to each other.

Each tensioning piston 24 further includes a suture attachment wheel 26 attached by means of an axle 28 to the tensioning piston 24. The suture attachment wheel 26 is able to rotate, and thereby self-adjust, after looped sutures have been tied and looped around the suture attachment wheel 26. This ability of the suture attachment wheel 26 to rotate ensures that equal tension is applied to each side of the looped suture. This, in turn, equalizes the tension applied to each end of a looped tissue graft strand.

A tension post 30 attached to the tensioning piston 24 extends through, and freely moves within, a tension indicator slot 32 within the cylinder module 22. The magnitude of the tensile load being applied to a soft tissue graft strand at any given time will be related to the location of the tension post 30 relative to the cylinder module 22. In order to more accurately determine the exact load being applied, graduations 33 may be provided on the cylinder module 22 at or near the tension indicator slot 32. The graduations 33 can provide any desired measuring standard, such as metric (e.g., Newtons) or English units (e.g., pounds), as well as any desired level of precision.

In order to adjust the tension applied by each adjustable tension applicator 18 or 20, a mechanism for selectively moving the cylinder module 22 towards or away from the tensioning piston 22 is provided. As seen in FIGS. 2 and 2A, each adjustable tension applicator 18 or 20 includes a tension adjustment knob 34 attached to a tension adjustment bolt 36 in threaded communication with the cylinder module 22. The tension adjustment bolt 36 passes through a pair of bolt holes 38 at the front and back ends of the tensioning block or module 16, respectively. The bolt holes 38 are not threaded and thus allow free rotation of the tension adjustment bolt 36 without changing the location of the tension adjustment bolt 36 relative to the tensioning module 16. For ease of use, and to conveniently extend the tension adjustment knobs 34 behind or beyond the tensioning pistons 24, knob extenders 39 may be provided as shown in both FIGS. 1 and 2.

Beyond each of holes 38, each tension adjustment bolt 36 is suspended within a cylinder block guide cavity 40, which holds and guides the cylinder module 22 as it slides back and forth relative to the tensioning block 16 and the tensioning piston 24. More particularly, a side tongue or extension 42 extending laterally from the bottom of the cylinder module 22 is able to slide back and forth within the cylinder block guide cavity 40. The side extension 42 of the cylinder module 22 further includes a threaded hole 44 in threaded communication with the tension adjustment bolt 36, which includes corresponding threads 46. The interaction between the adjustment bolt threads 46 and the threaded hole 44 of the cylinder module 22 provides for fine, adjustable movement of the cylinder module 22 relative to the tensioning piston 24 as the tension adjustment bolt 36 is selectively rotated, such as by means of the tension adjustment knob 34. The degree or magnitude of movement of the cylinder module 22 per revolution of the tension adjustment bolt 36 is dependent on the gauge of the threads 44 and 46.

As seen in FIGS. 2 and 2A, the tensioning piston 24 further includes a first piston end 48 having a first diameter and a second piston end 50 having a second diameter that is smaller than the diameter of the first piston end 48. A biasing spring 52 is circumferentially disposed around the second piston end 50 and makes abutment with an internal end face 54 of the first piston end 48. As better seen in FIG. 1, the tensioning piston 24 also includes a longitudinal guide pin hole 56 through which a guide pin can pass, if desired, during attachment of the tensioning device 10 to the patient's limb. The tensioning piston 24 also includes an attachment hole 58 into which the tension indicator pole 30, is mounted.

The cylinder module 22 includes an internal cylindrical hollow 60 having a diameter that is complementary to the diameter of the first piston end 48 so as to allow for slidable passage of the first piston end 48 therethrough as the cylinder module 22 is moved either towards or away from the tensioning piston 24. The cylinder module 22 further includes a smaller diameter end hole 62 sized so as to allow for slidable passage of the smaller diameter second piston end 50 therethrough as the cylinder module 22 is moved either towards or away from the tensioning piston 24. The biasing spring 52 that is circumferentially disposed around the smaller diameter second piston end 50 of the tensioning piston 24 makes abutment with an internal end face 64 of the internal cylindrical hollow 60 at the junction with the end hole 62.

Thus, the biasing spring 52 is maintained within the length or volume defined by the internal end face 64 of the internal cylindrical hollow 60 and the internal end face 54 of the fist piston end 48 of the tensioning piston 24. In this way, the biasing spring 52 becomes compressed as the cylinder module 22 is moved towards the tensioning piston 24 (as seen in FIG. 2A), thereby increasing the compressing force applied by the biasing spring 52 onto the tensioning piston 24, which is essentially equal to the tensile load applied by the tension piston 24 onto the soft tissue graft attached thereto.

The tensioning system 12 is advantageously attached to the patient's limb (e.g., the leg below the knee) by means of the limb attachment system 14. As seen in FIGS. 1, 2 and 2A, the limb attachment system 14 includes a limb attachment block or module that is matable with the tensioning block or module 16. The limb attachment module 66 further includes a pair of pin guides 72, each having a longitudinal guide pin hole 74 therethrough sized so as to accommodate a guide pin 76 (FIG. 3). The guide pins 76 can be driven, drilled or otherwise pushed into the bone of the patient's limb.

Once the guide pins 76 have been attached to the bone, the limb attachment module 66 can be conveniently slid on and off the guide pins 76 as desired. Once the attachment module 66 has been attached to the patient's limb, the tensioning system 12 can be attached to the limb attachment system 14. Even though the limb attachment module 66 is only slidably connected to the guide pins 76, the tensioning device 10 is held in place against the patient's limb by the countervailing tension exerted by the soft tissue graft being tensioned.

In an exemplary method for carrying out joint repair procedure, two or more strands comprising a soft tissue graft are harvested from the patient, such as from the ham strings or patellar tendon. In one embodiment, the semitendinous and gracillis are harvested from the patient's body. As shown in FIG. 3, the soft tissue graft may comprise a first soft tissue strand 100 and a second soft tissue strand 102. The ends of the soft tissue strands 100 and 102 opposite the free ends (or the ends where tension is to be applied) are attached at an appropriate location on the patient's bone comprising one of the bones of the joint. A looped tissue graft will include a pair of free ends. First graft attachment sutures 104 are attached to the free end(s) of the first soft tissue strand 100 and second graft attachment sutures 106 are attached to free end(s) of the second soft tissue strand 102. Each attachment suture 104 and 106 includes a pair of free ends tied together so as to form a loop, which is in turn looped around a corresponding suture attachment wheel 26. The suture attachment wheels 26, if allowed to freely rotate, equalize the tension applied to each side of looped sutures 104 and 106.

Figure 7:
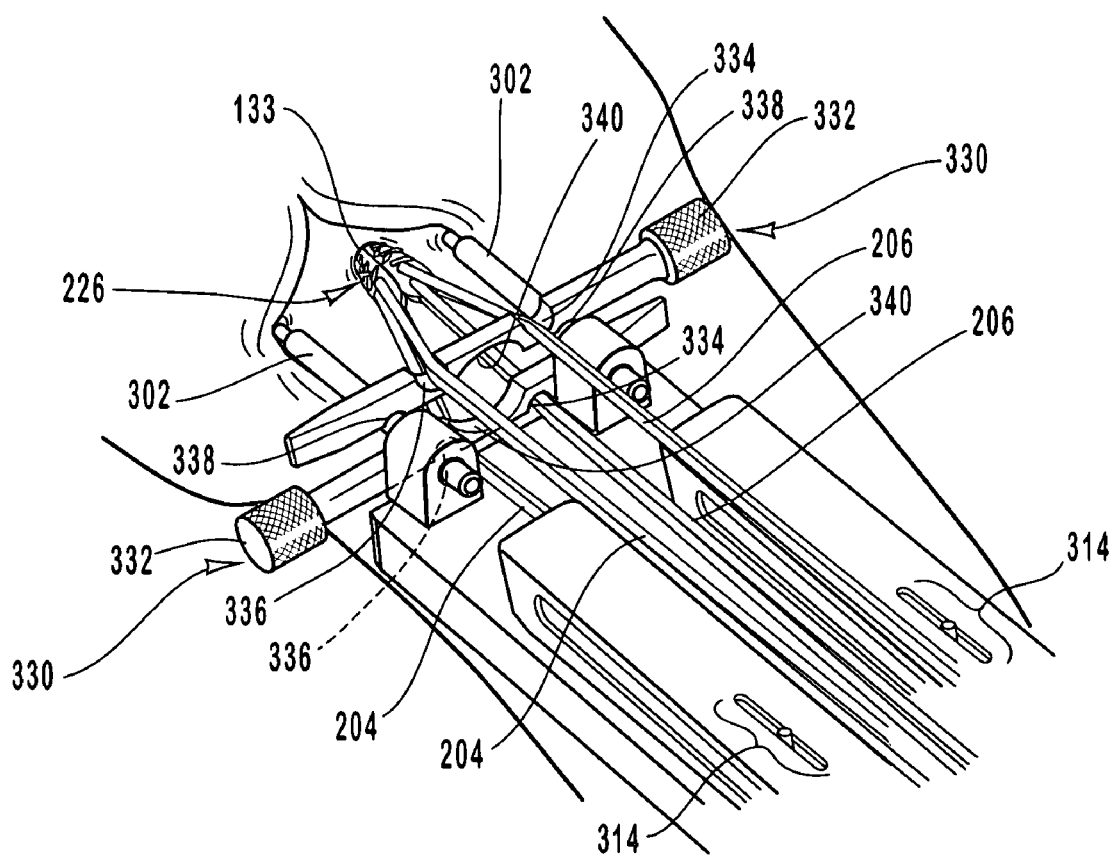
FIGS. 7 and 7A illustrate an embodiment of a suture separation and organization device used to separate and organize a plurality of suture strands into different defined regions.
Figure 8:
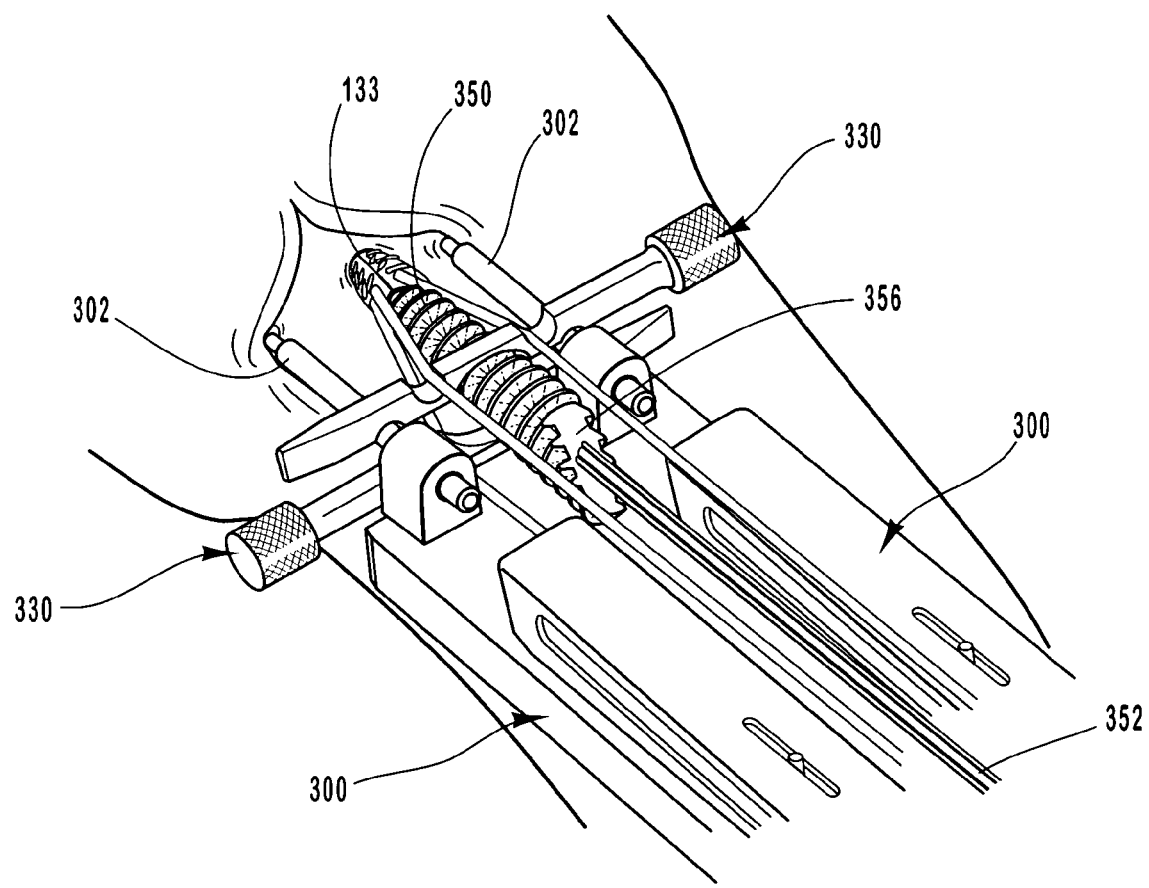
FIG. 8 illustrates the act of inserting an interference screw through a recess defined by the suture separation and organization device of FIGS. 7 and 7A and into the bone tunnel in order to secure the multiple-strand soft tissue graft against the bone tunnel wall.
Figure 9:
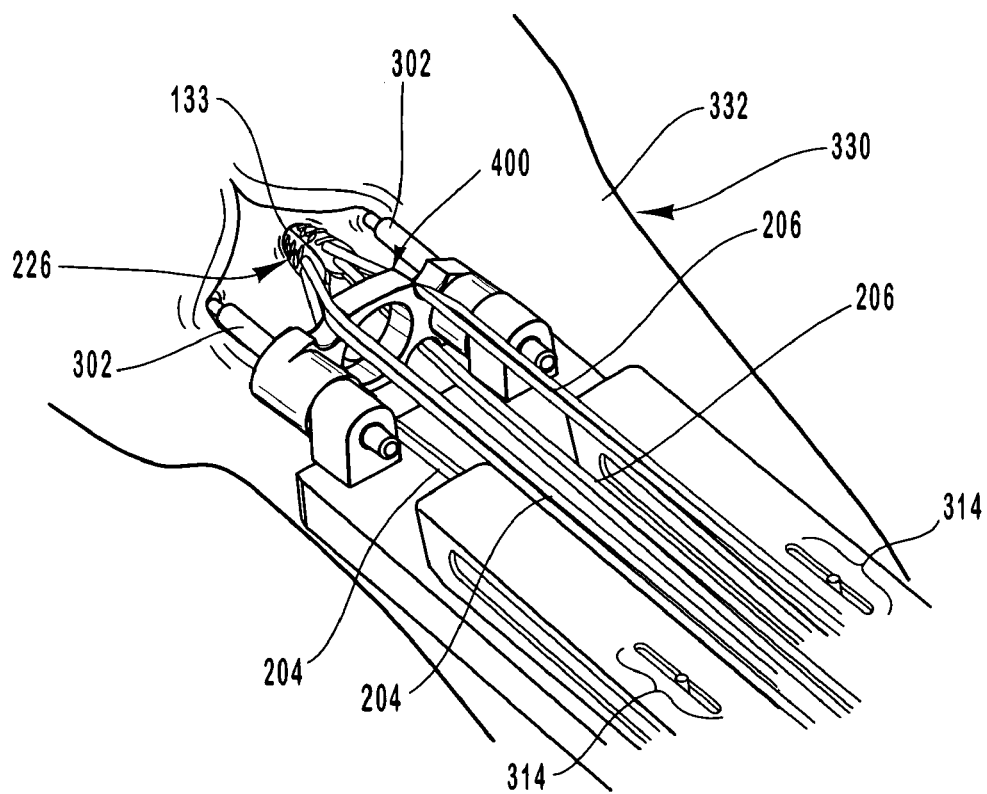
FIGS. 9, 9A and 9B illustrate an embodiment of a one-piece suture separation and organization device used to separate and organize a plurality of suture strands into different defined regions.
Figure 10:
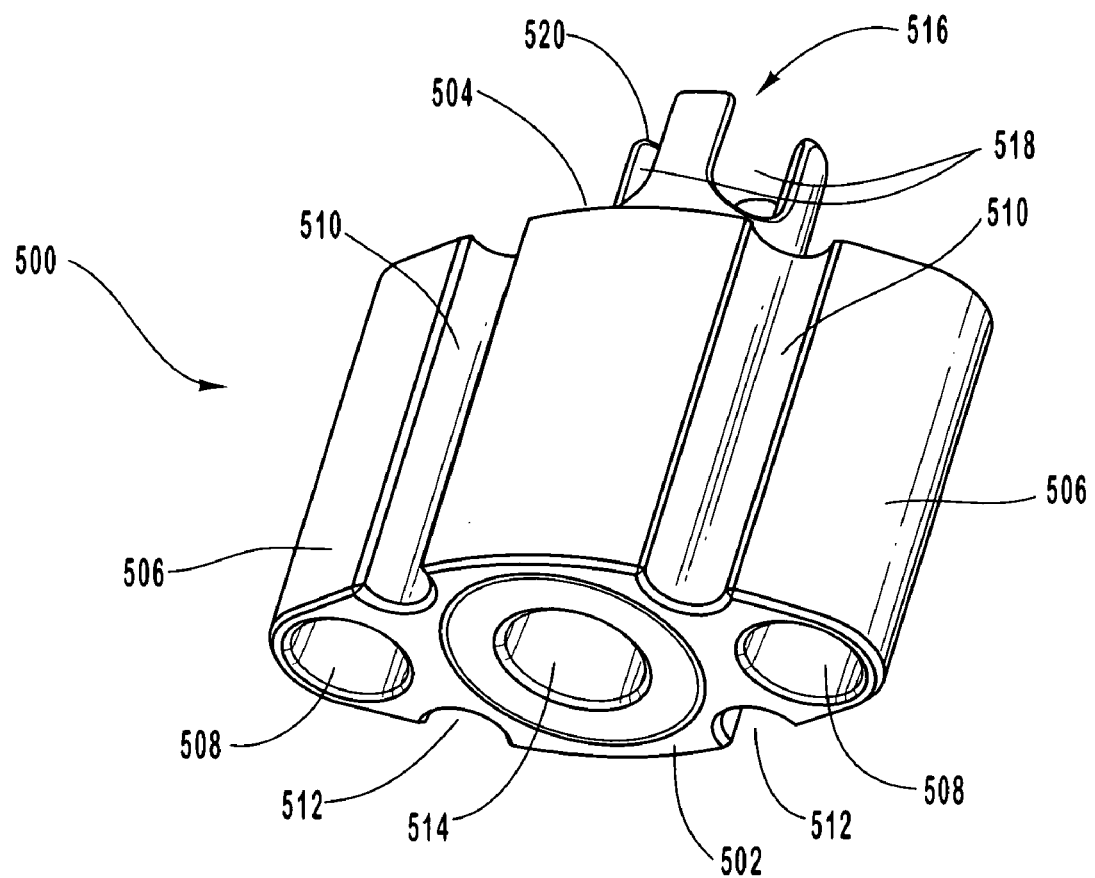
FIG. 10 depicts an alternative embodiment of a one-piece suture separator.

A suture separation and organization device according to the invention can be used to separate and organize graft attachment sutures 104 and 106. An exemplary two-piece suture separation and organization system comprising a pair of suture separation and organization devices 330 is depicted in FIGS. 7 and 8. Exemplary one-piece suture separation and organization devices are shown in FIGS. 9 and 10. Each of these devices will be discussed more fully below.

Each tension adjustment knob 34 is independently operated as desired to apply a desired tensile load to each of first and second soft tissue strands 100 and 102. The magnitude of the tensile load being applied to each soft tissue strand 100 and 102 can be measured by the displacement of each tension indicator pole 30 relative to its respective tension indicator slot 32, e.g., by referencing the location of each tension indicator pole 30 in relation to corresponding graduations 33 on the side of the corresponding tension indicator slot 32.

After the soft tissue strands 100 and 102 of the soft tissue graft have been properly conditioned and pre-tensioned, they are advantageously anchored or otherwise attached to the tibia 122. Anchoring may be accomplished, for example, by means of an interference screw (not shown). After securing the soft tissue strands 100 and 102 of the soft tissue graft to the tibia 122, the tensioning device 10 is removed by cutting or otherwise separating the sutures 104 and 106 from the suture attachment wheels 26 and then sliding the tensioning device 10 off of the guide pins 76. Thereafter, the guide pins 76 are removed from the patient's tibia by known surgical procedures.

Figure 4:
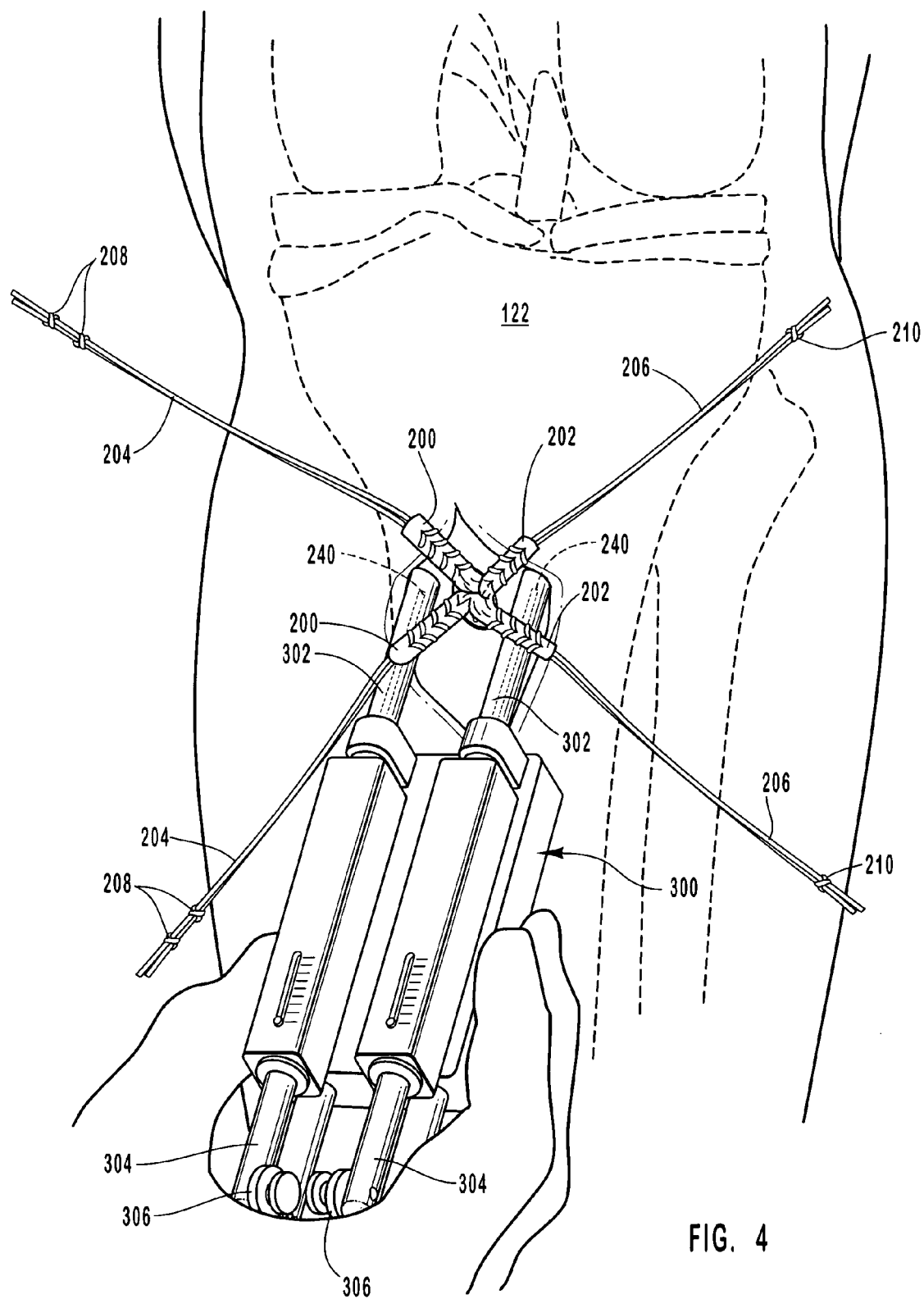
FIG. 4 shows another embodiment of a graft tensioning device attached to a patient's leg, and a soft tissue graft with attached sutures emerging from the bone tunnel.

FIG. 4 illustrates a non-modular graft tensioning device 300 positioned adjacent to a bone tunnel and attached to a pair of soft tissue graft strands 200 and 202. The tensioning device 300 includes a pair of hollow attachment posts 302 that are slidably inserted over a pair of guide pins 240 extending from the tibia 122. In this way the tensioning device 300 can be slidably connected to the guide pins 240. The free ends of the soft tissue graft strands 200 and 202 extend out from the tibial bone tunnel to corresponding suture strands 204, 206. Knots 208, 210 help identify to which of the grafts 200 or 202 the respective suture strands 204, 206 are attached.

Figure 5:
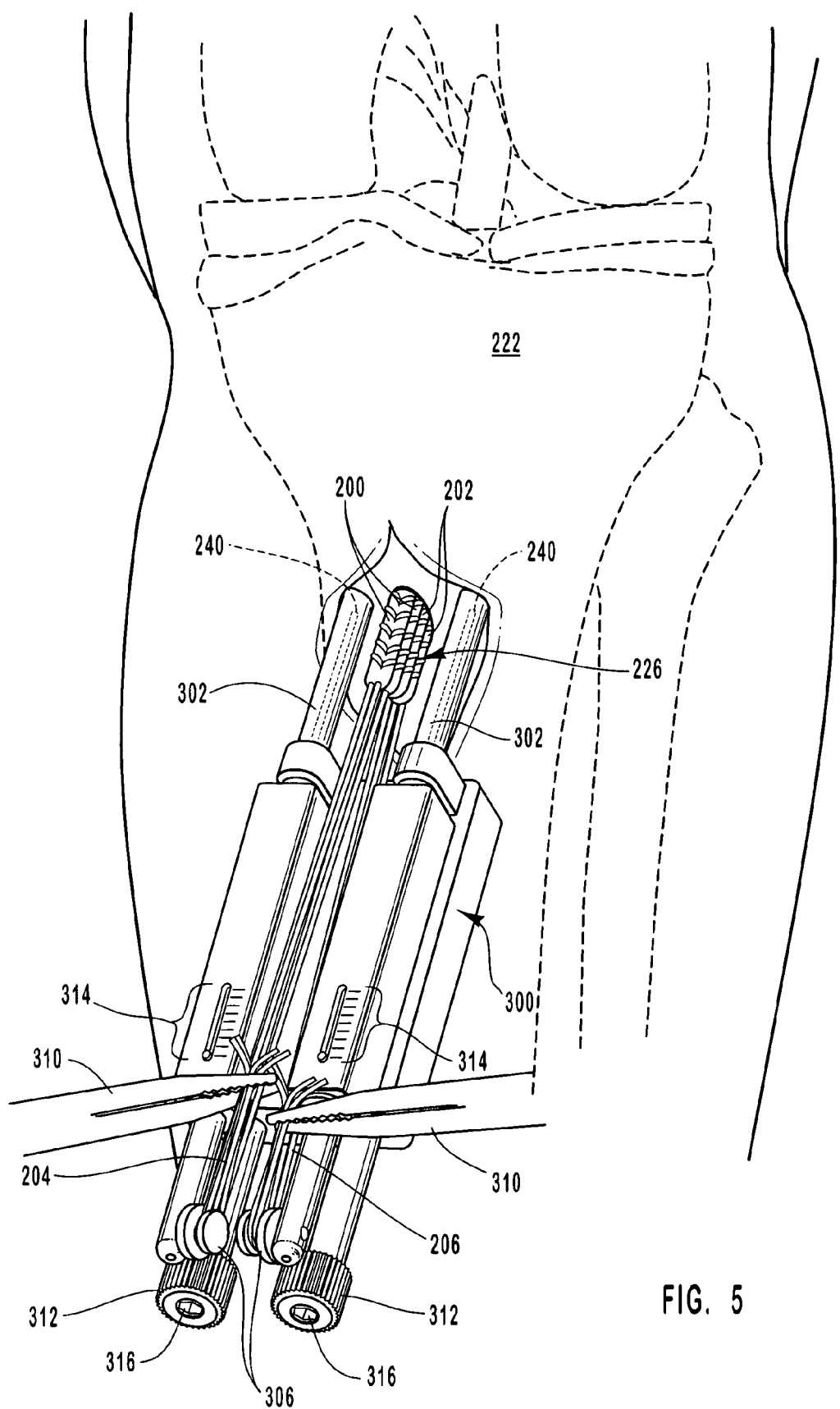
FIG. 5 shows a pair of sutures looped around respective suture pulleys of a graft tensioning device and being secured with suture clamps.

FIG. 5 depicts a method in which the suture strands 204, 206 are each clamped after being looped around a respective suture attachment pulley 306 by means of a respective suture clamp 310. If the suture clamps 310 are the only means of joining the free ends of the suture strands 204, 206 together, they may be left in place throughout the entire procedure until the free ends of the tissue graft strands 200, 202 have been secured to the tibia 122, e.g., within the tibial bone tunnel. The initially free ends of suture strands 204 and 206 may alternatively be tied together to form looped suture strands 204 and 206.

Figure 6:
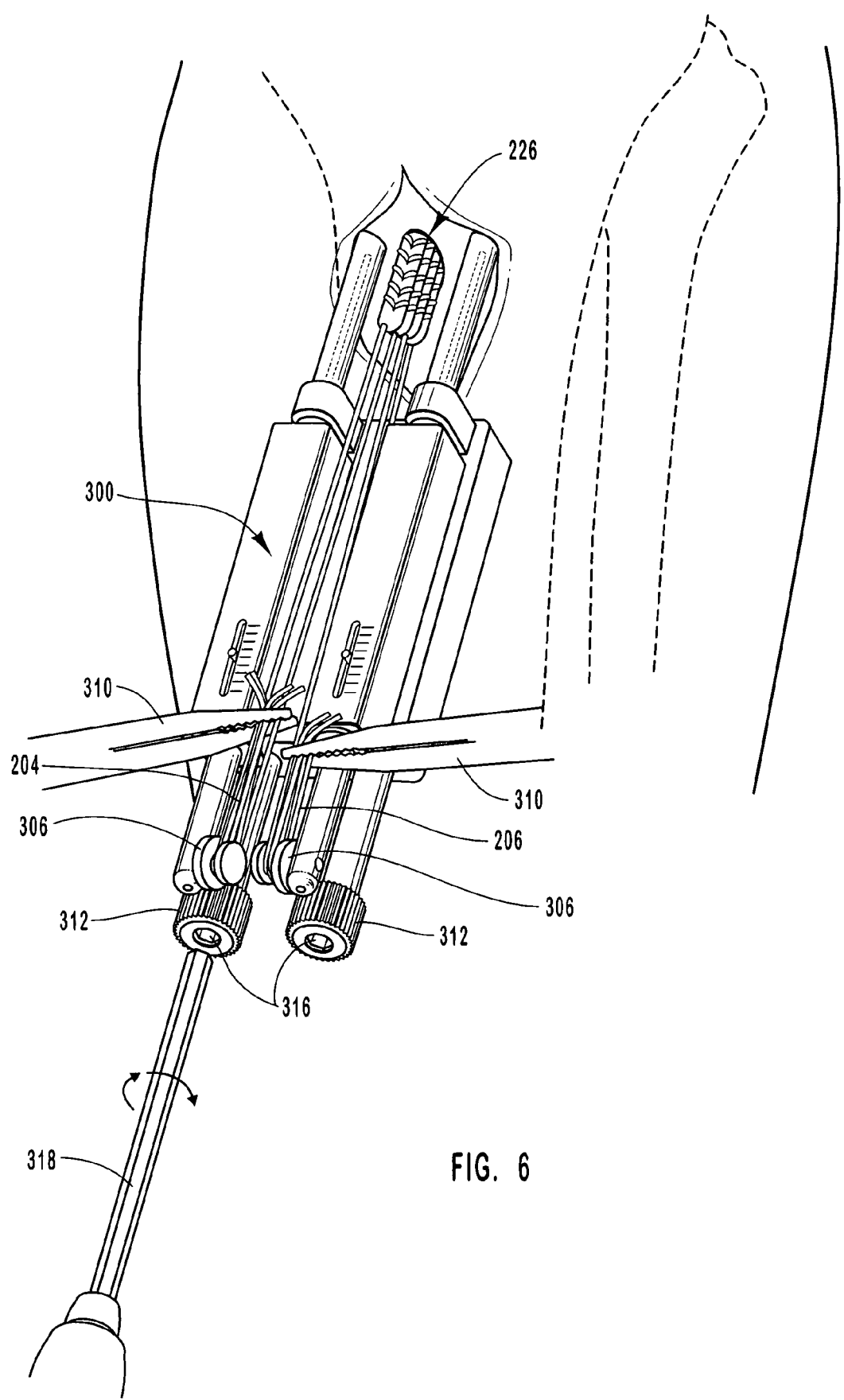
FIG. 6 shows the act of adjusting the tension applied to each looped suture by rotating an adjustment knob on the graft tensioning device.

The tensioning device 300 includes a pair of tension adjustment knobs 312, which interact with corresponding tensioning pistons 304 attached to the suture attachment wheels 306. By rotating the tension adjustment knobs 312, as illustrated in FIG. 6, an individualized tension or tensile stress can be separately applied to each soft tissue graft strand 200 and 202. The tension that is individually applied to each graft strand 200, 202 can be determined by viewing a tension gauge 314 associated with each tensioning piston 304. The tension adjustment knobs 312 may optionally include a hexagonal shaped recess 316 or other appropriate recess, protrusion, or other mechanical feature that permits attachment of a driver 318 to the tension adjustment knob 312. This assists the user in applying a desired level of tension.

According to one embodiment, as illustrated in FIG. 7, the suture strands 204, 206 can be separated into four quadrants by means of a pair of elongate suture separation and organization devices 330, which can be used alone or in tandem. This, in turn, provides more clear access to the tibial tunnel 133 for insertion of an interference screw (see FIG. 8). The use of suture separation and organization devices 330 also results in more even distribution of the four free, but yet unsecured, ends of the tissue graft strands 200, 202 around the perimeter of the tibial bone tunnel 133. Distributing the ends of the tissue graft strands 200, 202 over more of the surface area and perimeter of the tibial bone tunnel 133 results in a more concentric placement of an interference screw. This, in turn, is believed to result in a stronger final repaired joint, as the tissue graft strands 200, 202 make contact with more bone surface when they are concentrically positioned against the bone tunnel wall.

Figure 7A:
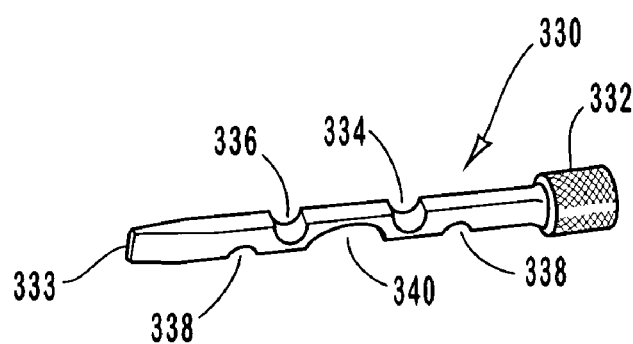

As shown more particularly in FIG. 7A, each suture separation and organization device 330 includes an elongate body comprising a gripping head 332 that aids in placing each suture separation and organization device 330 in a desired position relative to the tensioning device 300, more particularly, over and under the attachment posts 302 in a desired orientation and relative to suture strands 204, 206. The elongate body further comprises a chiseled end 333 that aids in inserting the suture separation and organization device 330 between two or more suture strands. The elongate body of co egg suture separation and organization device 330 is an example of body means for providing structure for the suture separation and organization device.

The suture separation and organization device 330 further includes a first suture retention recess 334 on the elongate body nearer the gripper head 332 into which one or more suture strands are placed and a second suture retention recess 336 on the elongate body nearer the chiseled end 333 into which one or more other suture strands are placed. Instead of first and second suture retention recesses 334 and 336, the suture separation and organization device 330 can alternatively include suture retention protrusions (not shown). Suture retention recesses and protrusions are examples of means for separating and organizing a plurality of suture strands in a desired spaced-apart orientation.

On the side of the elongate body of suture separation and organization device 330 opposite first and second suture retention recesses 334, 336 are a pair of guide recesses 338 that correspond to, and receive at least partially therein, attachment posts 302 of tensioning device 300 when in use. Guide recesses 338 are examples of means for removably attaching the elongate body of the suture separation and organization device 330 to a graft tensioning device.

Between the guide recesses 338 is a recess 340 through which an interference screw and driver can be inserted to affix the tissue graft to the tibia 122 when one or more suture separation and organization devices 330 are used and properly positioned. When two suture separation and organization devices 330 are used in tandem, the recess 340 of each device 330 together define a passageway through which an interference screw can be inserted during joint repair surgery.

In one embodiment, one suture separation and organization device 330 is placed on top of the attachment posts 302 in order to separate some of the suture strands into two upper quadrants, and a second suture separation and organization device 330 is placed under the attachment posts 302 in order to separate other suture strands into two lower quadrants. The mechanical engagement between the guide recesses 338 and attachment posts 302, in combination with an opposing force applied by the tensioned suture strands positioned within the suture retention recesses 334, 336, help lock each suture separation and organization device 330 in its desired position relative to the attachment posts 302.

After the suture separation and organization devices 330 have been properly positioned so as to distribute the suture strands into four quadrants, the conditioned and pre-tensioned tissue graft 226 is ready to be secured to the tibia 122 using any securing or anchoring means known in the art. As illustrated in FIG. 8, an interference screw 350 may be used. An interference screw 350 attached to an appropriate driver 352 is inserted through recesses 340 of the suture strand separators 330 and screwed into the tibial bone tunnel 133.

The interference screw 350 advantageously includes a recess designed to receive therein a correspondingly-shaped driving end of the driver 352. In one embodiment, the interference screw 350 may include an angled face 356 designed so as to lie substantially flush with the tibia when screwed into the tibial tunnel 133. This obviates the need to cut or remove part of the interference screw 350. It is, of course, within the scope of the invention to remove (e.g., by cutting) any excess portion of the interference screw 350 that extends beyond the tibia 122. Once the interference screw 350 or other securing means has been used to secure the tissue graft 226 to the tibia 122, the tensioning device 300 may be removed. The guide pins 240 are then removed and properly disposed of.

Figure 9A:
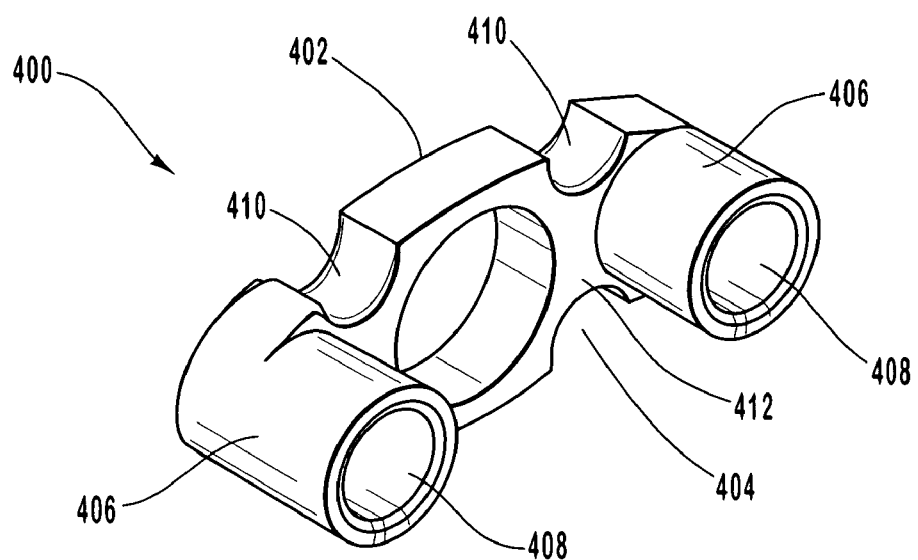
Figure 9B:
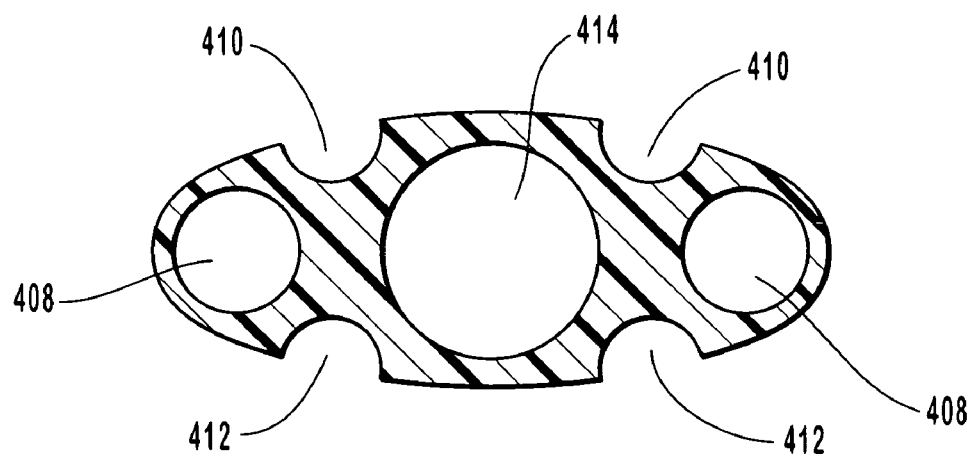

FIGS. 9, 9A, and 9B depict a one-piece suture separation and organization device 400 suitable for use with a graft tensioning device, or that together with a graft tensioning device comprises a graft tensioning system. The suture separation and organization device 400 includes a body having a first surface 402 that is oriented toward a graft tensioning device when in use and a second surface 404 that is oriented toward a bone tunnel in a patient's leg when in use. In this embodiment, the suture. separation and organization device 400 has a body with an approximate elliptical ellipsoidal cross section. Other cross-sectional shapes are within the scope of the invention. The body of suture separation and organization device 400 is an example of body means for providing structure for the suture separation and organization device.

The suture separation and organization device 400 further includes a pair of post guides 406 in a spaced-apart orientation and that include post-receiving passages 408 therethrough. The post guides 406 are sized and configured so as to receive within in passages 408 a pair of corresponding posts of a graft tensioning device (e.g., attachment posts 302 of tensioning device 300). Post guides 406 and passages 408 therethrough comprise examples of means for removably attaching the body of suture separation and organization device 400 to a graft tensioning device. The post guides 406 extend laterally from second surface 404 of the body in order to maintain space between the tensioning device 300 and the second surface 404 of the body when the suture separation and organization device is in use.

The suture separation and organization device 400 further includes a pair of suture retention recesses 410 disposed on one side of the perimeter of the body and another pair of suture retention recesses 412 disposed on an opposite side of the perimeter of the body. The suture retention recesses 410 and 412 are used to maintain a plurality of suture strands or groups of suture strands in a desired spaced-apart orientation relative to each other when the suture separation and organization device 400 is in use. In this embodiment, the suture strands or groups of suture strands are organized into four quadrants. It should be understood, however, that the suture separation and organization device 400 may include more or fewer suture retention recesses, or it may alternatively include suture retention protrusions (not shown). Suture retention recesses 410 and 412 (or suture retention protrusions, not shown) comprise examples of means for separating and organizing a plurality of suture strands in a desired spaced-apart orientation.

The suture separation and organization device 400 further includes a central passageway 414 that is sized and positioned so as to permit an interference screw to be inserted therethrough during joint repair surgery. In this way, the suture separation and organization device 400 is able to maintain the suture strands in the desired spaced-apart orientation while also permitting the surgeon to secure the soft tissue graft within the bone tunnel once the soft tissue graft has been conditioned and pretensioned in the desired manner.

FIG. 10 depicts an alternative suture separation and organization device 500 that also comprises a one-piece body that has a substantially elliptical or ellipsoidal cross section. The body of suture separation and organization device 500 further includes a first surface 502 that is oriented toward a graft tensioning device when in use and a second surface 504 that is oriented toward a bone tunnel in a patient's leg when in use. The suture separation and organization device further includes a pair of post guides 506 having post receiving passages 508 therethrough. The suture separation and organization device 500 also includes suture retention recesses 510 on a first side of the body perimeter and another pair of suture retention recesses 512 on an opposite side of the body perimeter. The suture separation and organization device 500 also includes a central passageway 514 through which an interference screw can be inserted during joint repair surgery. Suture separation and organization device 500 further includes an extension 516 that extends proximally toward the patient's leg when in use and that further includes a plurality of protrusions 518 (e.g., four) that define a plurality of recesses 520 therebetween (e.g., four) that can be used in organizing the ends of the soft tissue graft that emerge from the patient's bone tunnel during joint repair surgery.

The body of suture separation and organization device 500 comprises body means for providing a structure for the suture separation and organization device 500. Post guides 506 and passages 508 therethrough are examples of means for removably attaching the body of suture separation and organization device 500 to a graft tensioning device. The suture retention recesses 510 and 512 comprise means for separating and organizing a plurality of suture strands in a desired spaced-apart orientation.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suture separation and organization device for use in organizing and separating tensioned suture strands in a desired spaced-apart orientation during joint repair surgery, comprising:

a body having a first surface that is oriented toward a graft tensioning device when in use and second surface that is oriented toward a bone tunnel in a patient's leg when in use, the body having a center and a perimeter;

a plurality of attachment passages or recesses in said body for releasably attaching said body to a graft tensioning device during use, each passage or recess being sized and positioned so as to slidably receive therein a corresponding post of a graft tensioning device, each of said attachment passages or recesses being defined by a respective hollow post guide projecting from said second surface of said body so as to maintain space between a patient's leg and said second surface of said body when said suture separation and organization device is in use;

a pair of upper suture retention recesses or protrusions disposed on an upper perimeter of said body and a pair of lower retention recesses or protrusions disposed on a lower perimeter of said body, said pair of upper suture retention recesses or protrusions and said pair of lower suture retention recesses or protrusions being positioned so as to retain four tensioned suture strands or groups of tensioned suture strands extending away from a bone tunnel in four spaced apart quadrants adjacent to a bone tunnel in order to facilitate insertion of an interference screw between the tensioned suture strands and into the bone tunnel, said pair of upper suture retention recesses or protrusions being spaced apart and positioned so as to provide a first spacing distance between a pair of corresponding upper sutures, said pair of lower suture retention recesses or protrusions being spaced apart and positioned so as to provide a second spacing distance between a pair of corresponding lower sutures that is substantially equal to the first spacing distance; and a passageway or recess passing through the center of said body through which an interference screw can be inserted between tensioned suture strands during joint repair surgery.

2. A suture separation and organization device as defined in claim 1, said first surface of said body being substantially flat.

3. A suture separation and organization device as defined in claim 1, wherein each respective hollow post guide projects orthogonally from said second surface of said body.

4. A tensioning system for use in joint repair surgery, comprising:
  a suture separation and organization device according to claim 1; and
  a graft tensioning device configured so as to apply a desired tensile load to one or more soft tissue grafts emerging from a bone tunnel in a patient's limb and attached to a plurality of suture strands that extend away from the bone tunnel, said graft tensioning device including a plurality of posts designed so as to be slidably receivable through said attachment passages or recesses in said body of said suture separation and organization device.

5. A tensioning system for use in joint repair surgery according to claim 1, said graft tensioning device having adjustable tensioning means for selectively varying a tensile load applied to a plurality of suture strands attached to a soft tissue graft positioned within a bone tunnel and that extend away from the bone tunnel.

6. A suture separation and organization device as defined in claim 1, said passageway or recess passing through the center of said body being substantially cylindrical.

7. A tensioning system for applying variable tension to a plurality of suture strands attached to a soft tissue graft positioned within a bone tunnel and for organizing the suture strands preparatory to fastening the soft tissue graft within the bone tunnel, the tensioning system comprising:
  a graft tensioning device having adjustable tensioning means for selectively varying a tensile load applied to a plurality of suture strands attached to a soft tissue graft positioned within a bone tunnel and that extend away from the bone tunnel and means for removably attaching said graft tensioning device to a suture separation and organization device; and
  a suture separation and organization device comprising:
    body means for providing a structure for the suture separation and organization device;
    attachment means for removably attaching said body means to said graft tensioning device;
    a first plurality of upper suture retention recesses or protrusions disposed on an upper perimeter of said body means and a second plurality of lower retention recesses or protrusions disposed on a lower perimeter of said body means, said upper and lower suture retention recesses or protrusions being adapted to retain a plurality of tensioned suture strands or groups of tensioned suture strands extending away from a bone tunnel in a desired spaced-apart relationship on either side of the bone tunnel in order to facilitate insertion of an interference screw between the tensioned suture strands, said upper suture retention recesses or protrusions being spaced apart and positioned so as to provide a first spacing distance between a pair of corresponding upper sutures, said lower suture retention recesses or protrusions being spaced apart and positioned so as to provide a second spacing distance between a pair of corresponding lower sutures that is substantially equal to the first spacing distance; and
    a passageway or recess in said body means through which an interference screw can be inserted.

8. A tensioning system as defined in claim 7, said body means comprising a body having a first surface that is oriented toward a graft tensioning device when in use and second surface that is oriented toward a bone tunnel in a patient's leg when in use.

9. A tensioning system as defined in claim 8, said first surface of said body being substantially flat.

10. A tensioning system as defined in claim 8, said passageway or recess passing through a center of said body and being substantially cylindrical.

11. A tensioning system as defined in claim 8, said attachment means for removably attaching said body means to said graft tensioning device comprising a plurality of attachment passages or recesses in said body, each being sized and positioned so as to slidably receive therein a corresponding post of said graft tensioning device, said post comprising said means for removably attaching said graft tensioning device to a suture separation and organization device.

12. A tensioning system as defined in claim 11, each of said attachment passages or recesses being defined by a respective hollow post guide projecting from said second surface of said body so as to maintain space between a patient's leg and said second surface of said body when said suture separation and organization device is in use.

13. A tensioning system as defined in claim 7, said body means comprising:
  a first elongate body comprising a gripping head at one end and a chiseled end opposite said gripping head that facilitates insertion of said first elongate body between two or more suture strands, said first elongate body defining said upper perimeter of said body means; and
  a second elongate body similar or identical to, but separate from, said first elongate body, said first and second elongate bodies, when used in tandem, being adapted to separate and organize four suture strands or groups of suture strands into four spaced-apart quadrants, said second elongate body defining said lower perimeter of said body means.

14. A tensioning system for applying variable tension to a plurality of suture strands attached to a soft tissue graft positioned within a bone tunnel and for organizing the suture strands preparatory to fastening the soft tissue graft within the bone tunnel, the tensioning system comprising:
  a graft tensioning device having adjustable tensioning means for selectively varying a tensile load applied to a plurality of suture strands attached to a soft tissue graft positioned within a bone tunnel and that extend away from the bone tunnel; and
  a suture separation and organization device comprising:
    a first elongate body comprising a gripping head at one end and a chiseled end opposite said gripping head that facilitates insertion of said first elongate body between two or more suture strands, said first elongate body defining an upper perimeter of a composite body structure; and
    a second elongate body similar or identical to, but separate from, said first elongate body, said first and second elongate bodies, when used in tandem, being adapted to separate and organize four suture strands or groups of suture strands into four spaced-apart quadrants, said second elongate body defining a lower perimeter of said composite body structure;

attachment means for removably attaching said body means to said graft tensioning device;

a first plurality of suture retention recesses or protrusions disposed on an upper perimeter of said composite body structure and a second plurality of retention recesses or protrusions disposed on a lower perimeter of said composite body structure, said first and second pluralities of suture retention recesses or protrusions being adapted to retain a plurality of tensioned suture strands or groups of tensioned suture strands extending away from a bone tunnel in a desired spaced-apart relationship on either side of the bone tunnel in order to facilitate insertion of an interference screw between the tensioned suture strands; and a passageway or recess in said composite body structure through which an interference screw can be inserted.

15. A tensioning system for applying variable tension to a plurality of suture strands attached to a soft tissue graft positioned within a bone tunnel and for organizing the suture strands preparatory to fastening the soft tissue graft within the bone tunnel, the tensioning system comprising:

a graft tensioning device having adjustable tensioning apparatus for selectively varying a tensile load applied to a plurality of suture strands attached to a soft tissue graft positioned within a bone tunnel and that extend away from the bone tunnel and a plurality of posts for removably attaching said graft tensioning device to a suture separation and organization device; and a suture separation and organization device comprising:
a body;
a plurality of attachment passages or recesses in said body for removably attaching said body to said graft tensioning device, each being sized and positioned so as to slidably receive therein a corresponding post of said graft tensioning device;
a first plurality of upper suture retention recesses or protrusions disposed on an upper perimeter of said body and a second plurality of lower retention recesses or protrusions disposed on a lower perimeter of said body, said upper and lower suture retention recesses or protrusions being adapted to retain a plurality of tensioned suture strands or groups of tensioned suture strands extending away from a bone tunnel in a desired spaced-apart relationship on either side of the bone tunnel in order to facilitate insertion of an interference screw between the tensioned suture strands, said upper suture retention recesses or protrusions being spaced apart and positioned so as to provide a first spacing distance between a pair of corresponding upper sutures, said lower suture retention recesses or protrusions being spaced apart and positioned so as to provide a second spacing distance between a pair of corresponding lower sutures that is substantially equal to the first spacing distance; and
a passageway or recess in said body through which an interference screw can be inserted.

* * * * *

UNITED STATES PATENT AND TRADEMARK OFFICE
CERTIFICATE OF CORRECTION

PATENT NO. : 7,686,810 B2 Page 1 of 2
APPLICATION NO. : 10/786186
DATED : March 30, 2010
INVENTOR(S) : West, Jr. et al.

It is certified that error appears in the above-identified patent and that said Letters Patent is hereby corrected as shown below:

Drawings
Sheet 2, replace Figure 2 and 2A with the figure depicted below, wherein 16 is shown.
Sheet 2, replace Figure 2A with the figure depicted below, wherein 34 is shown.

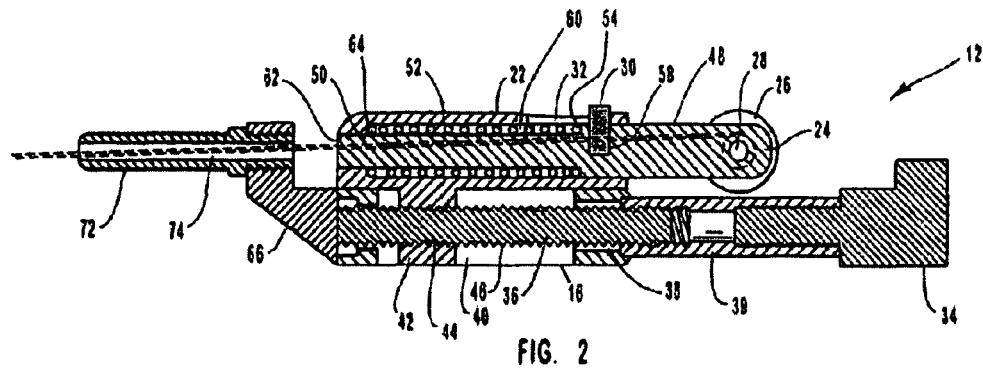

FIG. 2

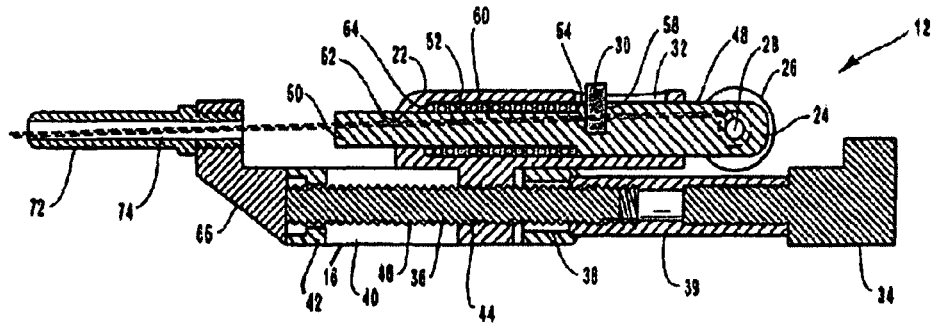

FIG. 2A

Signed and Sealed this

Twenty-fourth Day of August, 2010

David J. Kappos
Director of the United States Patent and Trademark Office

CERTIFICATE OF CORRECTION (continued)
U.S. Pat. No. 7,686,810 B2

Sheet 9, replace Figure 9A with the figure depicted below, wherein 414 is labeled.
Sheet 9, replace Figure 9A with the figure depicted below, wherein the line connecting 412 to the drawing is made shorter.

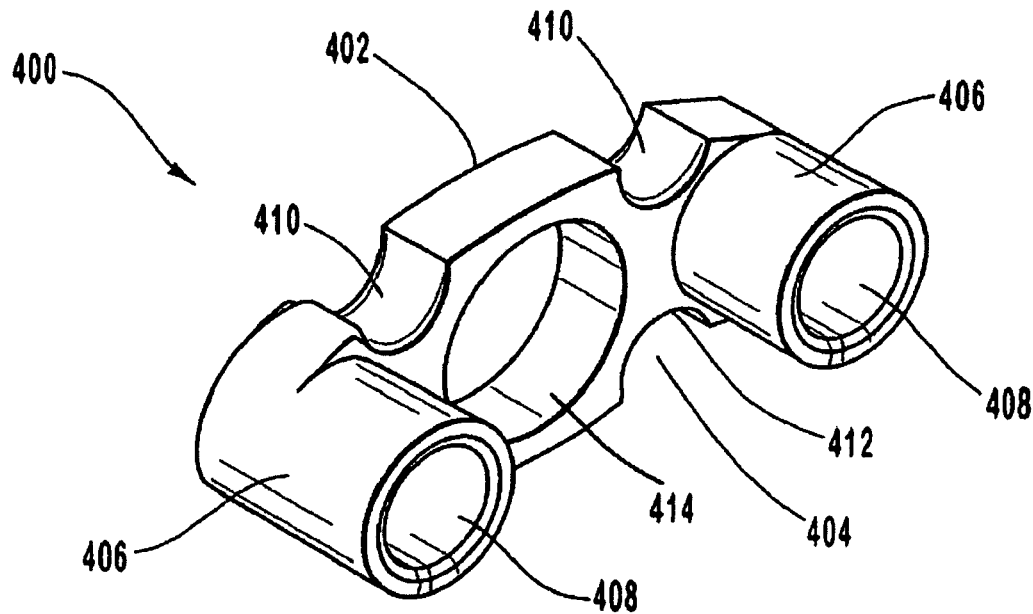

FIG. 9A

Column 3
Line 9, change "separates" to --separates,--.

Column 5
Line 11, change "22" to --24--.
Line 27, change "block" to --module--.